United States Patent [19]

Guerriero

[11] Patent Number: 4,742,822

[45] Date of Patent: May 10, 1988

[54] BUILT AROUND BODY ATTITUDE IMMOBILIZATION AND TRANSPORTATION DEVICE

[76] Inventor: Federico Guerriero, 1212 N. Lake Shore Dr., Chicago, Ill. 60010

[21] Appl. No.: 827,058

[22] Filed: Feb. 7, 1986

[51] Int. Cl.$^4$ ............................................. A61G 1/00
[52] U.S. Cl. ................................ 128/134; 128/87 R; 5/82 R
[58] Field of Search .................... 128/133, 134, 87 R, 128/85, 86, 88, 68, 78, 70, 71; 5/82 R, 424; 269/322, 328

[56] References Cited

U.S. PATENT DOCUMENTS

| | | | |
|---|---|---|---|
| Re. 28,620 | 11/1975 | Jordan et al. | 5/82 R |
| 2,417,378 | 3/1947 | Robinson | 5/82 R |
| 3,336,060 | 8/1967 | Bradford | 5/82 R |
| 3,648,305 | 3/1972 | Ersek | 5/82 R X |
| 3,671,983 | 6/1972 | Bertolek | 5/82 |
| 4,386,605 | 6/1983 | Wong | 128/134 |
| 4,463,752 | 8/1984 | Liao | 128/87 R |

Primary Examiner—Richard J. Johnson
Attorney, Agent, or Firm—A. R. Thiele

[57] ABSTRACT

A transport and immobilization device for a human patient having a fractured spinal vertebrae has an adjustable frame and a network of flexible straps attached to the adjustable frame which both bear the weight of the victim and immobilize the spinal column. The device will accommodate a wide variety of victim sizes, weights and orientations.

29 Claims, 9 Drawing Sheets

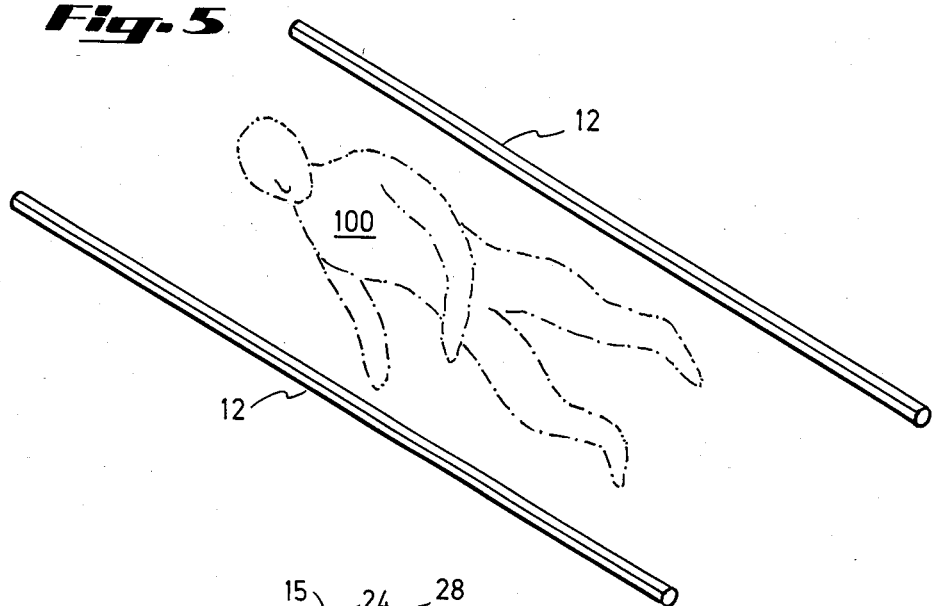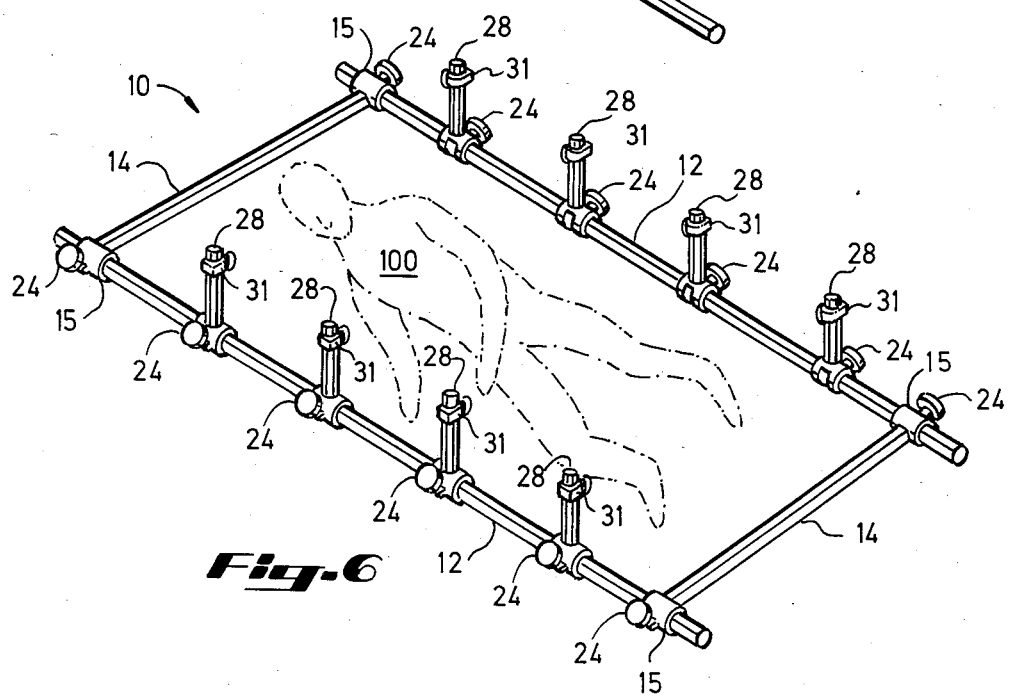

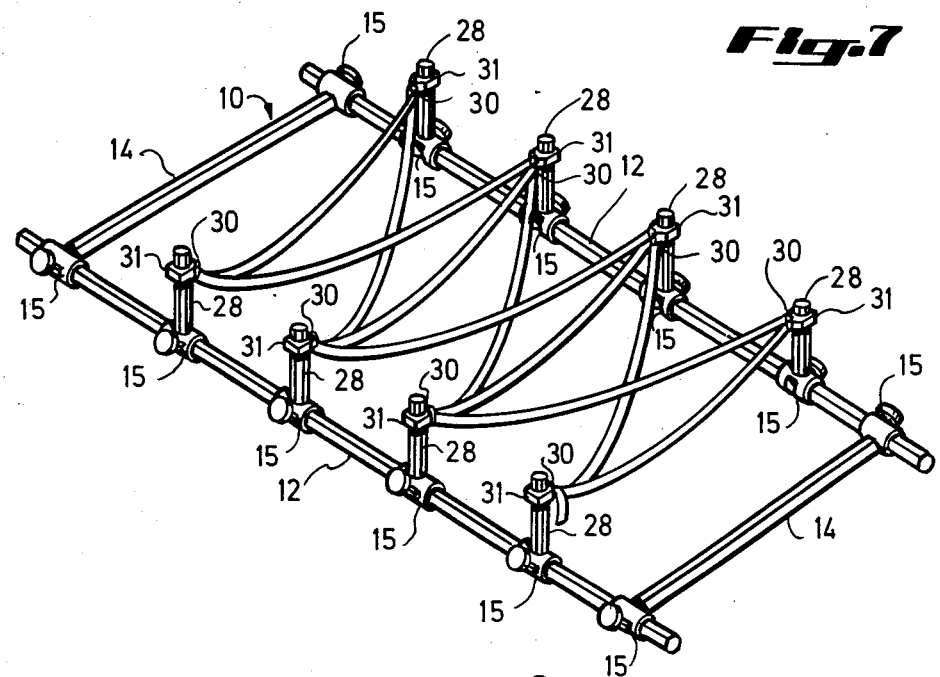
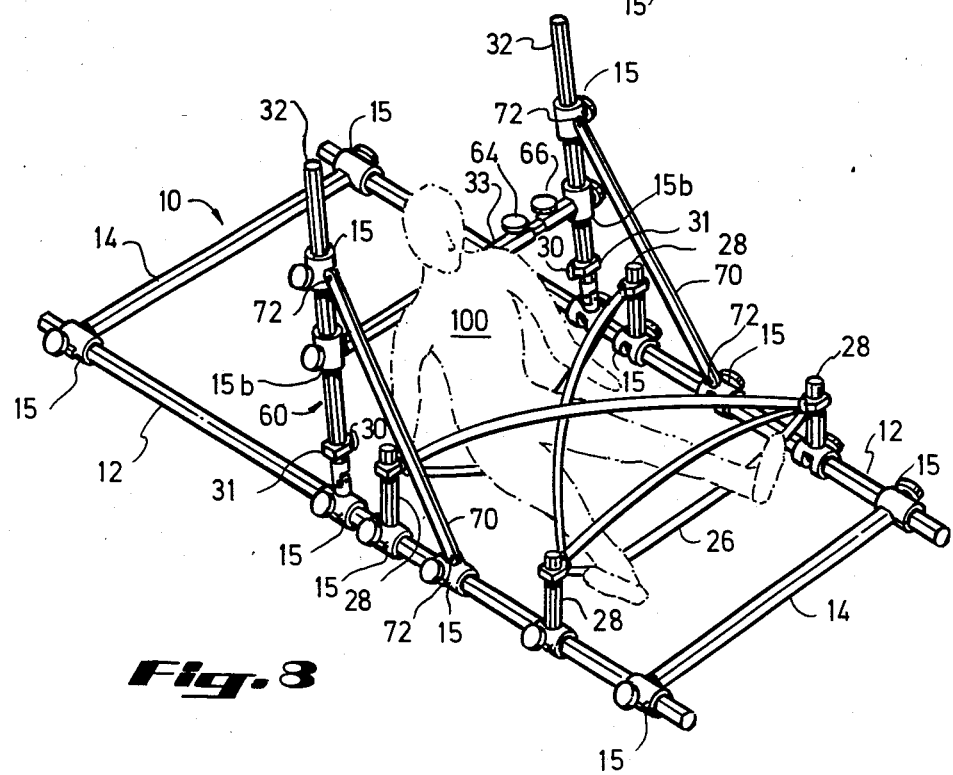

BUILT AROUND BODY ATTITUDE IMMOBILIZATION AND TRANSPORTATION DEVICE

BACKGROUND OF THE INVENTION

The present invention relates to a device and method for the pick-up and transport of accident victims having a suspected spinal fracture. More specifically, the invention relates to a device for the immobilization of the spinal column of an accident victim during pick-up and transport.

When a victim with a suspected spinal injury, specifically a fractured vertebrae, is found at the scene of an accident it is important that the victim be picked-up and transported so that the edges of any fractured vertebrae are immobilized. This immobilization of the vertebrae is necessary to prevent movement of any bone fragments during the evacuation of the patient. Without such immobilization the spinal cord may be severed or damaged by contact with the edges of the broken vertebrae as they relocate themselves within the spinal column. Such contact of the spinal cord with broken vertebrae may result in further injury far more severe than that resulting solely from the accident.

When the victim's body is found in either a sitting or a twisted position the natural tendency is to cause the victim to lay in a horizontal position typically on a spinal or back board to protect the spine. This simple action, while well intended, does not protect the spinal cord. In fact, it may do just the opposite, it may cause additional and potentially more severe injury. The key to this concept involves the understanding that the ideal treatment for a spinal injury victim would involve immediate repositioning of the broken vertebrae so that the integrity of the spinal cord would not be put in jeopardy. Such re-positioning of the broken vertebrae, in order to be properly performed, must be done at a medical facility with the benefit of x-ray imagery. X-ray imagery will assure that the spinal cord is not damaged by the sharp edges of broken vertebrae during the repositioning manipulation. Each movement of the spinal column must be carefully monitored to assure that the spinal cord is fully protected. Clearly, the fewer the manipulations of the bone fragments in the spinal column, the lesser the chance for injury to the spinal cord. The intermediate re-orientation of a victim's body at the scene of an accident from the position resulting from the effects of an accident to a prone position resulting from the placement of the victim's body on a stretcher or backboard may result in an improper and dangerous intermediate manipulation of the bone fragments within the spinal column. The elimination of such intermediate manipulations would markedly reduce the chance for injury to the spinal cord.

Sitting or twisted body positions are often associated with victims of automobile accidents. If the automobile accident has caused the spinal cord to move near the jagged edge of a broken vertebrae, even the slightest movement of the fractured pieces of the broken vertebrae may sever, pinch or damage the spinal cord. Such slight movement of the bone fragments may occur when the body position of the victim is changed, even a very small amount. Typically, body position changes occur when emergency medical treatment personnel remove the victim from an automobile for placement on a transport device, such as a backboard, canvas stretcher or wheeled cot.

Despite the good intentions of emergency medical technicians or ambulance crews accident victims may be injured a second time by the movement or grinding of the segments of the broken vertebrae. Such movement or grinding may result in physical damage to the spinal cord itself or to the vessels supplying blood to the spinal cord. This second injury to the spine may have consequences far more severe than those resulting from the initial fracture of the vertebrae. Such consequences may be total paralysis or death. Therefore a need exists in the art to provide a device which will both immobilize the spinal column in the position assumed after the accident and also provide for the transportation of a victim with suspected broken vertebrae in the same attitude as found, thereby eliminating any dangerous and unneeded intermediate manipulations of the spinal column.

It must also be recognized that accident victims vary greatly in weight and size. Therefore, a further need exists in the art to provide a spinal immobilization and transport device that can accommodate a wide range of victim weights and sizes, while still affording complete immobilization of the spinal column during transport away from the accident scene.

Present methods of victim transport used by emergency or paramedical personnel include the placement of a "short backboard" or "long backboard" underneath a victim with a suspected injury to the spinal column.

The "long backboard" is used where the patient is found in a prone or in a semisitting position. To place the patient on a "long backboard" the first step involves physically lifting the victim. This simple act of lifting can cause dangerous internal movement of the bone fragments thus affecting the unprotected spinal cord and its blood supply. Such movement within the spinal column dramatically increases the potential for further injury. If the patient is caused to lie flat on the backboard, there is yet additional inter-spinal motion and the enhanced potential for severe injury.

For a spinal injury victim whose transport involves movement from a sitting position, such as in an automobile, there is also a false apprehension that proper transport of the patient can be obtained by use of a "short backboard". If the victim must be removed from the automobile any force on the pelvis of the patient may cause motion in the spinal column particularly at the point of fracture; hence the potential for greater injury caused by contact of the bone fragments with the spinal cord or its blood supply.

Once the patient has been moved to a medical care facility the patient must be moved again. This movement usually involves the lifting of the victim to a bed by 4 to 6 people who endeavor to lift the victim in unison. Any slight variation from a unison lift can cause further injury to the vertebrae or damage to the spinal cord by movement of the vertebrae fragments within the spinal column.

It is therefore an advantage of the built around body attitude immobilization and transport device and method of the present invention to enable both the transport of a victim with a suspected spinal fracture and the immobilization of the spinal column irrespective of body position, body attitude or body configuration.

It is yet an additional advantage of the present invention to provide a device which may be easily assembled and readily transported by emergency medical personnel.

It is still a further advantage of the device of the present invention to provide a transportation system and method which will prevent movement of bone fragments within the spinal column irrespective of the victim's size or weight.

SUMMARY OF THE INVENTION

The built around body attitude transportation device and method of the present invention consists of two basic parts. The first part is an assemblage of rigid members which are constructed around the victim to form an adjustable frame. The second part is a network of flexible straps which is interlaced within the adjustable frame to both immobilize the spinal column and support the body weight of the victim. This immobilization of the entire spinal column causes the edges of the fractured vertebrae to not move with respect to the spinal cord during the lifting, moving and transport of the victim to a medical care facility.

The adjustable frame consists of two side support rails which are readily affixed together by releasable jaw couplings. Positioned on the side support rails are a plurality of adjustable ring posts. The adjustable ring posts are mounted to the side support rails by releasable jaw couplings and are used to provide tie points for the network of flexible straps which is subsequently formed around the victim and attached to the adjustable frame.

The network of flexible straps is formed within the adjustable frame by interlacing the straps around the trunk and extremities of the victim. Once the network is complete the victim becomes an intregral part of the adjustable frame and strap network. With the patient completely laced into the device, removal and transportation of the victim from the scene of an accident is facilitated while at the same time immobilizing the broken pieces of the vertebrae thus preventing further injury to the spinal cord.

BRIEF DESCRIPTION OF THE DRAWINGS

A further understanding of the built around body attitude immobilization and transportation device and method of the present invention may be had by reference to the drawings wherein:

FIGS. 5, 6 and 7 illustrate the construction of the device of the present invention around a spinal injury victim found in the prone position;

FIGS. 8 and 9 illustrate construction of the device around a spinal injury victim found in the sitting position;

DETAILED DESCRIPTION OF THE EMBODIMENTS OF THE INVENTION

Figure 1:
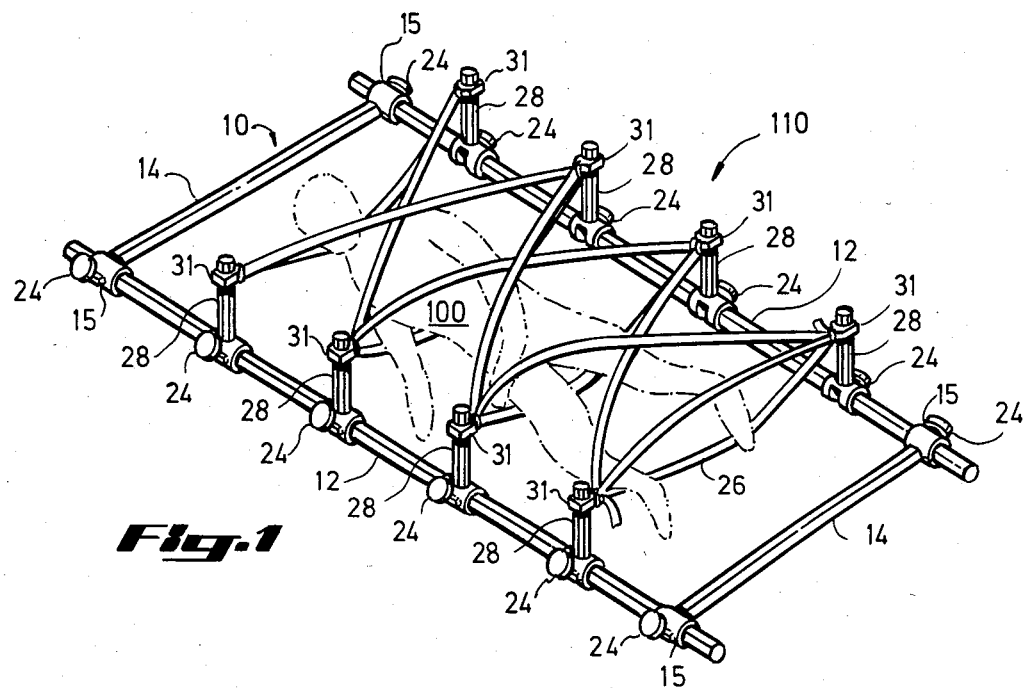
FIG. 1 is a perspective view of the device of the present invention assembled about a spinal injury victim found in the prone position.
Figure 2:
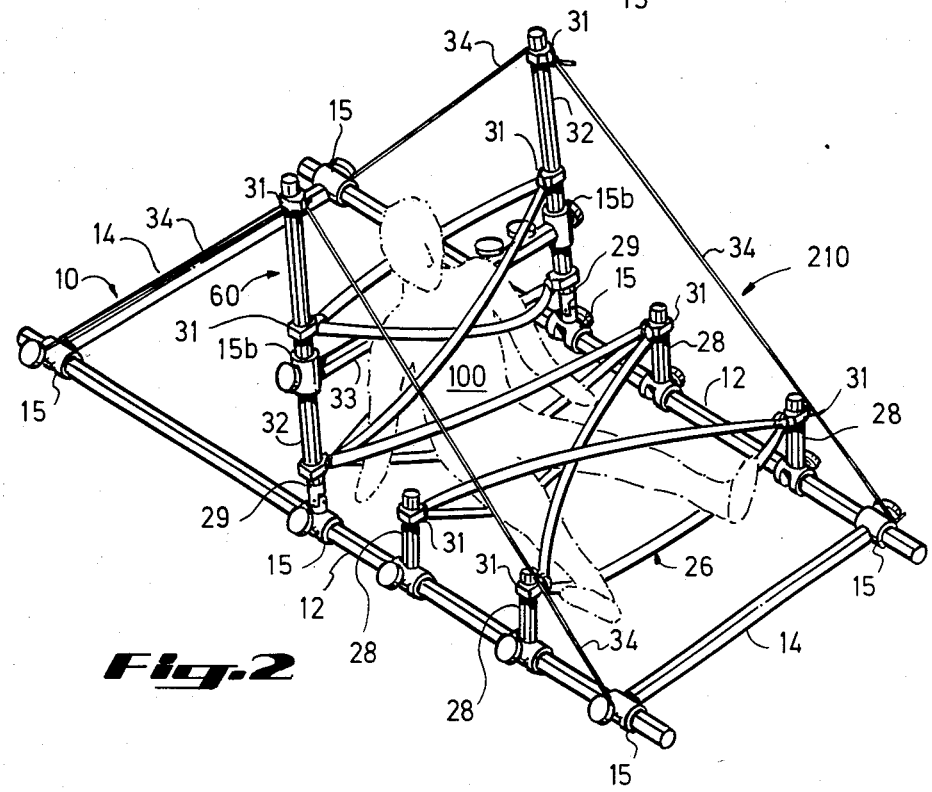
FIG. 2 is a perspective view of the device of the present invention assembled about a spinal injury victim found in the sitting position.
Figure 3:
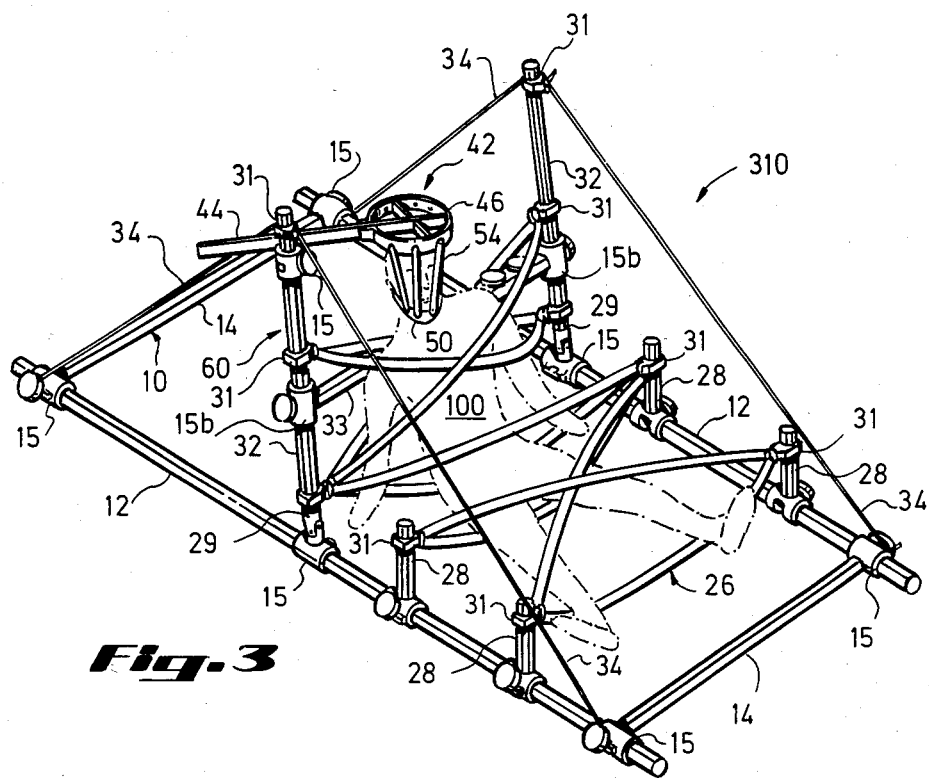
FIG. 3 is a perspective view of the device of the present invention assembled about a spinal injury victim further providing for immobilization of the victim's head.
Figure 4:
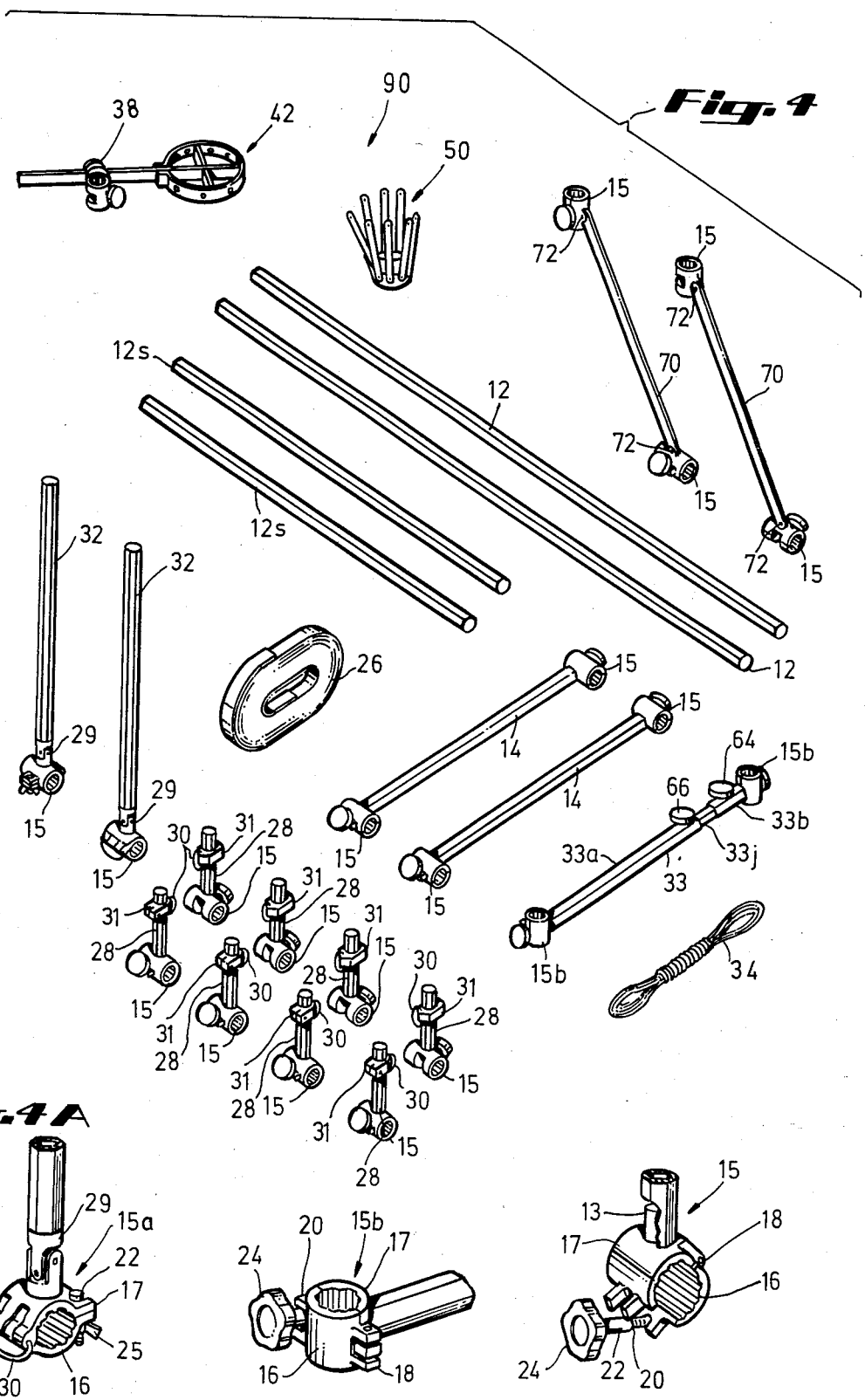
FIG. 4 is a disassembled array of the various components used to assemble the built around body attitude transportation device.

As shown in FIGS. 1, 2 and 3 the device of the present invention may be assembled in three different configurations 110, 210, 310 depending upon the position, attitude or configuration in which the victim 100 is found at the scene of an accident. Emergency medical personnel will construct the various embodiments described herein by selecting components as needed from kit 90 consisting of a variety of different sized basic components as shown in FIG. 4.

In FIG. 1 it may be seen that device 110 may be used for transporting a spinal injury victim 100 found in a prone position. Device 110 consists of two essential parts. The first part, an adjustable frame 10 is constructed from two rigid side support rails 12 and two rigid end support rails 14. It will be understood that a variety of sizes of side support rails 12 and end support rails 14 may be provided in kit 90 (FIG. 4) for emergency medical personnel to accommodate victims 100 of varying weights and sizes. In the preferred embodiment hollow hexagonal tubing is used to form rails 12 and 14; however, any shape lightweight rigid tubing may be used without affecting the operability of devices 110, 210 or 310.

Figures 4A, 4B:
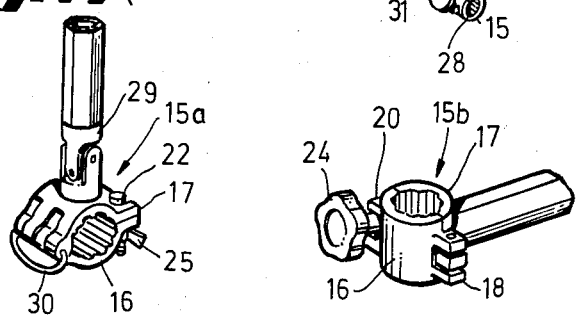
FIGS. 4A, 4B and 4C are detailed views of representative releasable jaw couplings.
Figure 4C:
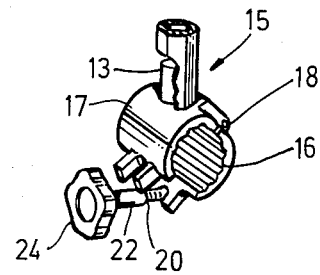

End support rails 14 are attached to side support rails 12 to form a rectangle around the victim 100. The corners of the rectangle are formed by releasable jaw couplings 15 which may be attached to the hollow tubing as shown in FIG. 4C. Specifically, there is shown an interference fit of a solid member 13 inside the hollow portion of the tubing. These releasable jaw couplings 25 consist of a lower jaw 16 which is connected to an upper jaw 18 by hinge 17. Hinged upper jaw 18 includes "U" shaped screw receptacle 20 for receipt of threaded rod 22. Threaded rod 22 is hingedly affixed to lower jaw 16 on one end and is provided with knob 24 or alternatively a wing nut 25 on its opposite end. When it is desired to secure lower jaw 16 to upper jaw 18, threaded rod 22 is positioned in "U" shaped screw receptacle 20. Knob 24 is then turned so that the bottom of knob 24 is held in frictional contact with the top of "U" shaped receptacle 20. This will hold upper jaw 18 and lower jaw 16 together. If desired cam activation or any other type of quick acting mechanical method of attaching side rails 12 to end rails 14 may be used on couplings 15 without affecting the operability of the device. Shown in FIGS. 4A and 4B are modified jaw couplings. In FIG. 4A a jaw coupling is shown which includes a wing nut 25, a universal joint 29 and ring 30. Shown in FIG. 4B is jaw coupling 15b that is substantially similar to jaw coupling 15 in FIG. 4C except that the orientation of knob 24 is diametrically opposed to that shown in FIG. 4C.

With reference again to FIG. 1, extending upwardly from side support rails 12 are adjustable ring posts 28. In the preferred embodiment ring posts 28 are releasably mounted to side support rails 12 by the same type of couplings 15 (FIG. 4C) that are used to mount end support rails 14 to side support rails 12. Rings 30 may be attached to ring posts 28 by couplings 31. Couplings 31 are substantially the same as couplings 15a (FIG. 4A) with universal joint 29 eliminated. If desired, rings 30 may be rigidly mounted to ring posts 28.

As shown in FIGS. 1, 2 and 3, a plurality of ring posts 28 are placed at convenient locations along each side support rail 12. It is not necessary that ring posts 28 be spaced in an equidistant manner along side rails 12 nor is it necessary that an equal number of ring posts 28 be used on each side rail 12. In the illustrated embodiments 110, 210 and 310 an equal number of ring posts 28 are shown on each side; however, any number of ring posts 28 may be used. It will be understood that the number of ring posts 28 employed depends on the weight, size or position of the victim 100. While ring posts 28 are used in the preferred embodiment it will be understood that ring posts 28 may be eliminated without affecting the operability of the invention, as explained below.

When adjustable frame 10 has been constructed around the victim and ring posts 28 have been positioned on side support rails 12 a network of high strength woven straps 26 is formed over and under the victim's body 100 by interlacing flexible straps 26 between rings 30. This network of straps 26 is formed to provide support for the torso and extremities of victim 100. It is preferred to form a high density network of straps under the victim 100 to support the pelvic area of victim 100 and a lesser density network of straps to support the extremities of victim 100. It will be understood that the straps which pass under the victim 100 and support the weight of the victim 100 are most important. Those straps which pass over the victim may be eliminated in an emergency situation.

While high strength woven straps 26 are used in the preferred embodiment, ropes or similar material may be used without affecting the operability of the built around body attitude device. If desired, straps 26 may be tied directly to side support rails 12 or ring posts 28; however, it is been found that the use of rings 30 facilitates the forming of strap network 26.

In FIG. 2, embodiment 210 is specially adapted from embodiment 110 for a victim found in the sitting position. This adaptation of frame 10 is effected by the addition of upright support frame 60 to what now may be termed lower frame 10. Upright frame 60 is releasably mounted to side support rails 12 by releasable couplings 15 of the type shown in FIG. 4C which include a universal joint 29 (FIG. 4A) attached to solid member 13 projecting from the side of coupling 15.

Frame 60 is constructed from upright support rails 32 and extensible, rotatable crosspieces 33. As may be best seen in that portion of FIG. 4 which illustrates extensible, rotatable crosspiece 33, crosspiece 33 is formed in two sections 33a and 33b which meet at junction 33j. Set screws 64 and 66 permit the locking of sections 33a and 33b one with respect to the other at junction 33j. At the outer ends of extensible, rotatable crosspieces 33 are releasable jaw couplings 15b as shown in FIG. 4B. One or more crosspieces 33 may be used depending on the size and orientation of the body of victim 100.

The angular position of upright support rails 32 with respect to side support rails 12 is provided by universal joint 29. Rails 32 are held in their proper angular position with respect to side rails 12 by rope 34 which is affixed to support rails 32 and side rails 12 on either side of frame 10. Alternatively, brace member 70 may be used in place of rope 34 as shown in FIGS. 8, 9, 10 and 11. Brace member 70 is characterized by having jaw couplings 15 at either end which include pin mounting points 72.

Upright support rails 32 may also include ring couplings 31 of the same type as used on ring posts 28. Rings 30 on ring couplings 31 may be used to receive straps 26 which have been passed around the body of victim 100 for lacing the upper portion or torso of victim 100 into upright support frame 60. They may also be used as mounting points for rope 34.

Figure 3A:
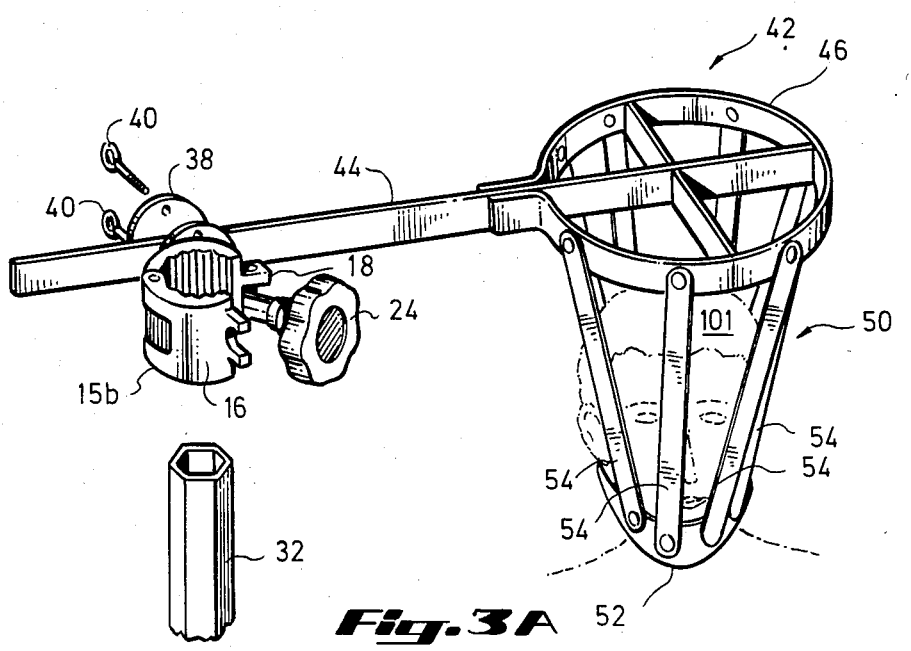
FIG. 3A is an enlarged perspective view of the head restraint system.
Figure 3C:
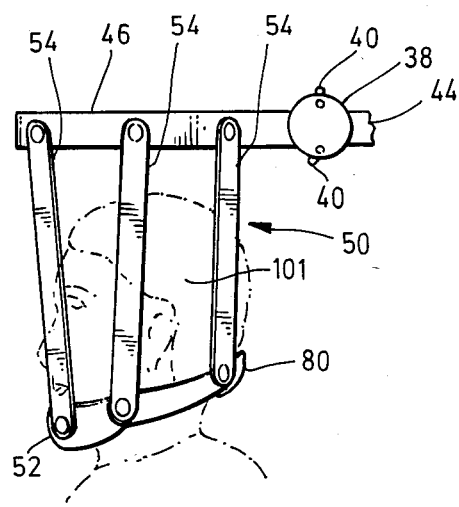
FIG. 3C is a view in side elevation of the head restraint system.
Figure 3B:
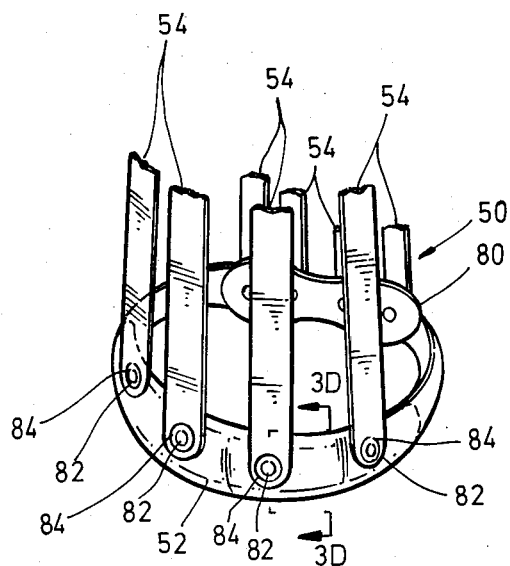
FIG. 3B is a detailed view of the lower portion of the head restraint system.
Figure 3D:
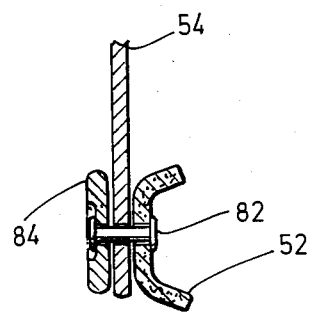
FIG. 3D is a view taken along line 3D—3D of FIG. 3B.

In FIG. 3 embodiment 310 shows the modification to embodiment 210 resulting from the addition of head support assembly 42 to upright support frame 60. As shown in FIG. 3A, head support assembly 42 consists of arm 44 and circular portion 46. Assembly 42 is used by positioning circular portion 46 over the head 101 of victim 100. As may be seen with reference to FIGS. 3B, 3C and 3D assembly 42 provides the mounting for flexible head support 50. Head support 50 consists of a flexible chin support piece 52, nape support 80 and risers 54. Risers 54 may be attached to chin support piece 52, nape support 80 and circular portion 46 by the use of a rivet 82 and button 84 combination as shown in FIG. 3D. Alternatively, cord or rope may be used in place of risers 54. Such core or rope can be laced through holes formed in circular portion 46, chin piece 52 and nape support 80 if desired.

Figure 3E:
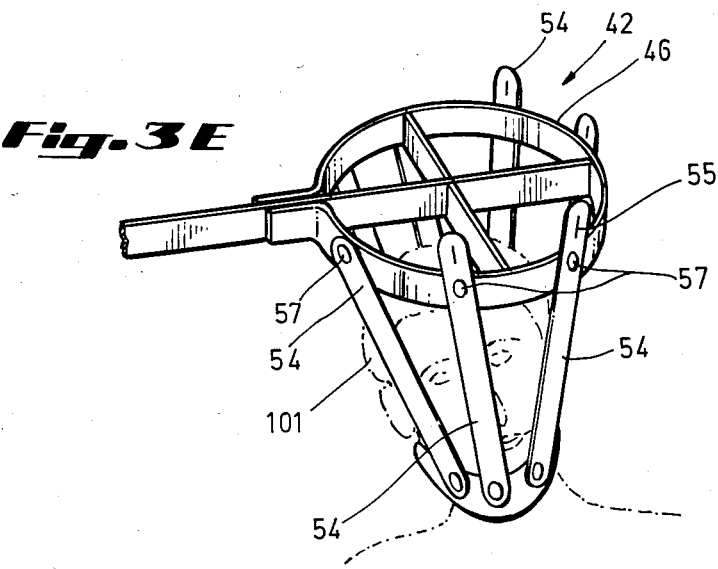
FIG. 3E is a view similar to FIG. 3A showing the victim's head slightly tilted to one side.
Figure 3F:
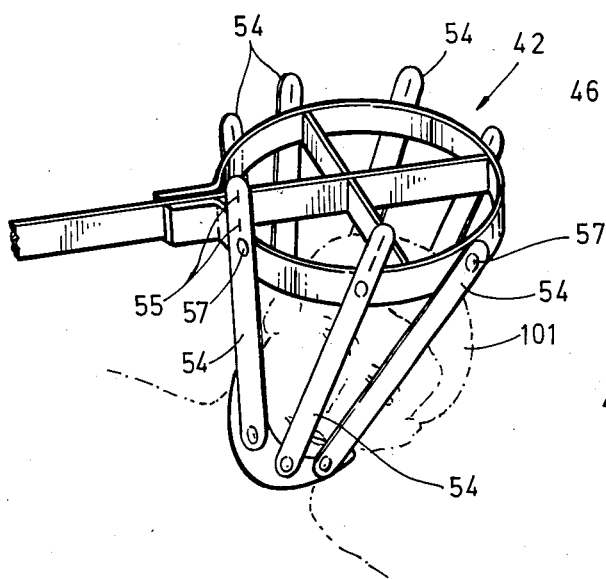
FIG. 3F is a view similar to FIG. 3A showing the victim's head severely tilted to one side.

If the head 101 is tilted to one side or the other, to the front or to the back or along a diagonal, the risers 54 may be adjusted as shown in FIGS. 3E and 3F. Specifically, as shown in FIG. 3E head 101 is shown slightly tilted to the right. Risers 54 on the victim's left have been forshortened to hold head 101 in place. In FIG. 3F head 101 is severely tilted to the back and to the right. Herein risers 54 have been forshortened to an even greater extent for the purpose of immobilizing head 101 of victim 101 in the position found at the scene of the accident. Accordingly, the head of a victim is immobilized in any desired positioning by the shortening or lengthening of risers between circular portion 46 and chin support piece 52 and nape support 80.

While head support assembly 42 is shown for illustrative purposes with embodiment 210, it is understood that it may be used with embodiment 110 by attaching it to side rail 12.

Operation of the Device

The initial step in the operation of the built around body attitude transportation device of this invention is placement of side support rails 12 generally parallel to the longitudinal orientation of the victim 100 as shown in FIG. 5. In the example illustrated by FIG. 5 the victim 100 has been found in the prone position.

As seen in FIG. 6 end support rails 14 are placed between side support rails 12 then affixed to side support rails 12 to form a rectangular frame 10 around victim 100 by placing side support rails 12 between upper jaw 18 and lower jaw 16 of releasable jaw coupling 15 (FIG. 4C) at each of the four corners. Screw 22 is placed within "U" shaped screw receptacle 20 and knob 24 is turned so as to secure upper jaw 18 against lower jaw 16.

A plurality of ring posts 28 with ring clamps 31 attached are then positioned along side support rails 12 by the use of releasable couplings 15 (FIG. 4C). A sufficient number of ring posts 28 are attached to span the length of the victim 100 and form the basis for the network of straps 26 which is used for support and immobilization of victim 100. It will be understood that while ring posts 28 are shown in the preferred embodiment, straps 26 may be tied directly to side rails 12.

As shown in FIG. 7 straps 26 are interlaced between rings 30. It will be understood that in FIG. 7 victim 100 is not shown in order to illustrate the formation of the network of straps 26; however, with victim 100 in place the straps are passed over and under the victim's body 100 and extremities as shown in FIG. 1.

Particular attention should be given to supporting the pelvic area of victim 100 with strap network 26 and also to immobilizing the torso of the victim 100 to prevent injury to the spinal cord when victim 100 is lifted and moved by the built around body attitude device of the present invention. Where necessary straps 26 may be slid under the victim by means of wrapping or attaching straps 26 to the end of a flat stick or prod. Straps 26 are affixed to ring 30 by a knot or other suitable method of attachment.

Once the interlacing of victim 100 within frame 10 is complete as shown in FIG. 1, the entire frame assembly with prone victim 100 immobilized therein is lifted and carried in the same manner as a canvas stretcher. In this manner the victim's spinal column will be immobilized while the victim is being removed from the scene of the accident and transported to a medical care facility.

If victim 100 happens to be found in a sitting position as shown in FIG. 8 the same type of rectangular frame 10 is constructed as was shown in FIG. 1; however, an upright support frame 60 is created and mounted on frame 10.

Figure 9:
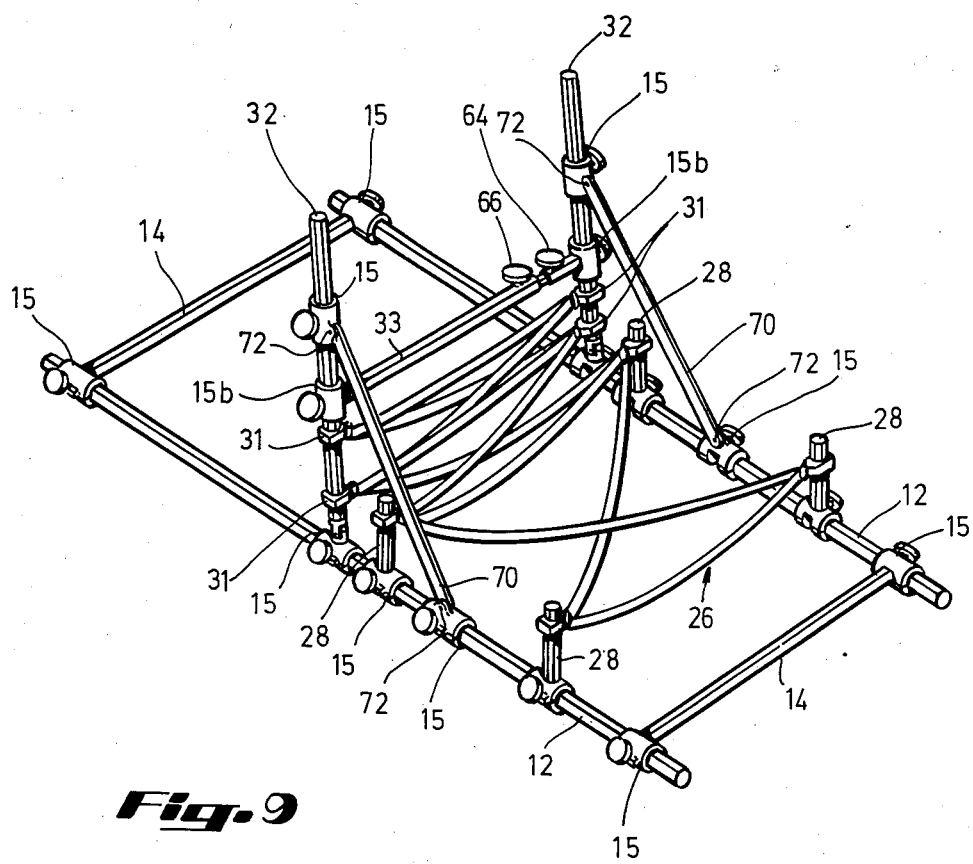
Figure 11:
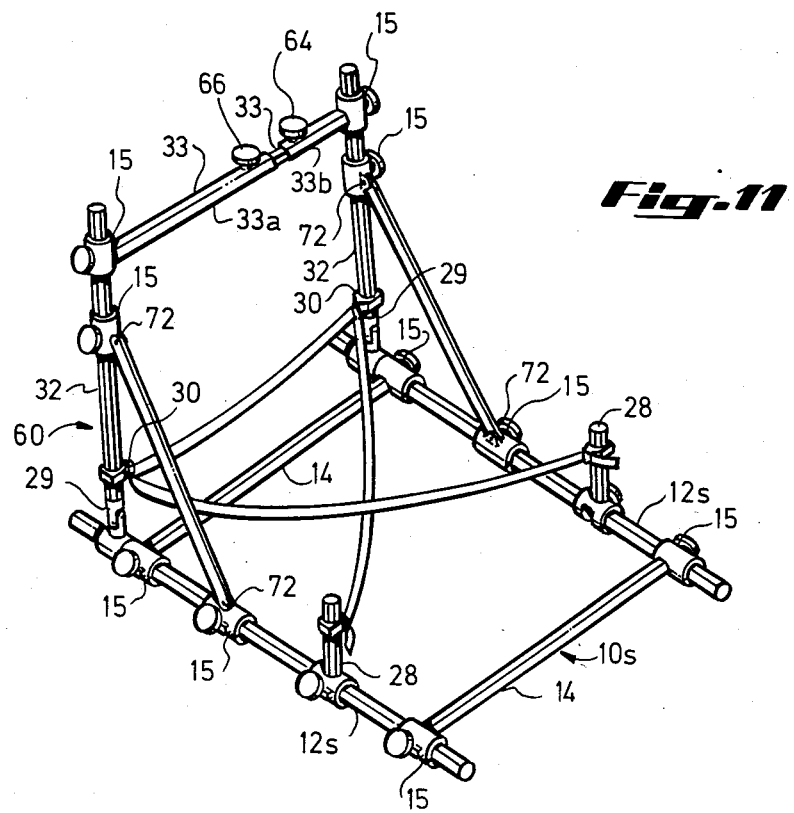
FIG. 11 is a perspective view of another embodiment of the device of the present invention adapted for use with patients found in a sitting position in a confined space such as an automobile.

In FIG. 11 it will be seen that frame 10 may be adapted for a victim found sitting in a confined space such as in an automobile. Accordingly, frame 10s includes only the pelvic and hip area within its planar confines (FIG. 8). This is accomplished by the use of short side rails 12s with end rails 14. The upper torso of victim 100 is then interlaced into the upright frame 60 with straps 26 to immobilize the victim's back before transport as shown in FIG. 9. Upright frame 60 is similar to that shown in FIGS. 2, 3, 8 and 9 and is formed by affixing upright rails 32 to side support rails 12 with releasable couplings 15 having universal joint 29. Correct positioning of frame 60 with respect to the back of victim 100 is accomplished by adjusting extensible, rotatable crosspiece 33 and brace members 70.

If the back of victim 100 is twisted so too may upright frame 60 be twisted with respect to side support rails 12 to match the orientation of the back of victim 100. This twisting of frame 60 is accomplished by adjusting upright rails 32 at different angles with respect to side support rails 12. Universal joints 29 give rails 32 the required range of positions. By sliding couplings 15 on either end of brace member 70 along upright rails 32 and side rails 12, respectively, frame 60 may be locked in position.

When upright rails 32 have been properly positioned behind the victim's back they are connected together by extensible, rotatable crosspieces 33. One or more crosspieces 33 are affixed to upright rails 32 by use of releasable couplings 15 and they may be slightly extended or turned in order to be mounted to upright rails 32. This is accomplished by the division of crosspieces 33 into two sections, 33a and 33b. These two sections 33a and 33b may be slightly separated and rotated one with respect to the other. When crosspiece 33 is sized to fit between upright rails 32 set screws 64 and 66 are used to lock pieces 33a and 33b together. Strap network 26 is now interlaced between rings 30 on upright rails 32 and then around the torso of the victim so as to entwine the victim in a network of straps 26 formed between upright rails 32. This interlacing of straps 26 around victim 100 will immobilize the spine of victim 100. With the lower extremities interlaced within frame 10 the victim 100 may now be picked up and transported to a hospital in the same sitting position in which he was found at the scene of the accident without risking any danger of injury to the spinal cord by movement of the vertebrae fragments.

Figure 10:
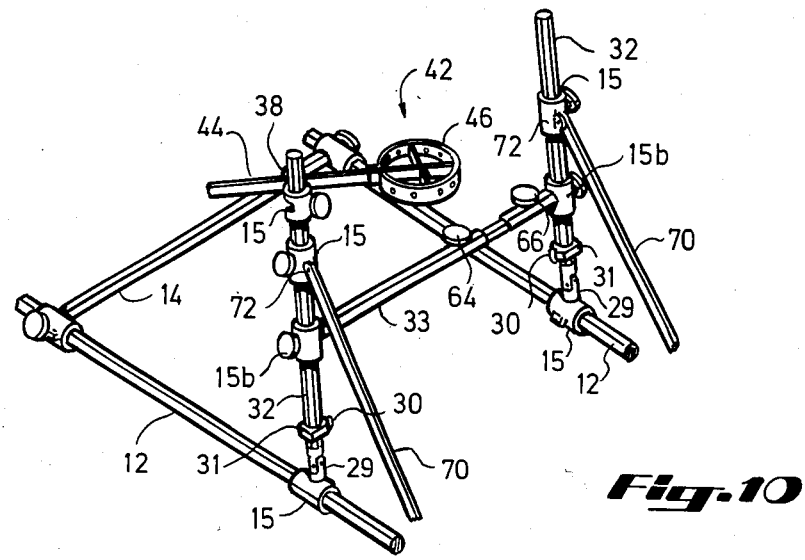
FIG. 10 is a partial perspective view of the device as shown in FIGS. 8 and 9 with the addition of the head restraining attachment.

In FIG. 10 yet another capability of the built around body attitude transport and immobilization device and method of the present invention is shown. This additional capability is used if the victim's head and neck must be immobilized before transport. Herein immobilization of the head 101 of the victim 100 is accomplished by the use of a head support assembly 42 which is affixed to either upright support rail 32 by means of a jaw coupling 15 and sandwich clamp 38 (FIG. 3A) actuated by clamp knobs 40. As shown in FIG. 3A, circular portion 46 of head support assembly 42 is positioned over the victim's head 101. The risers 54 of head support harness 50 are attached to the circular portion 46 of head support assembly 41. Chin support piece 52 and nape piece 80 immobilize head 101 of victim 100 when head support assembly 42 is positioned so that risers 54 are in tension. Risers 54 are made adjustable by the provision of several slots 55 through which buttons 57 may pass as shown in FIGS. 3E and 3F.

The strength and rigidity of side support rails 12, end support rails 14 and the other rail components which make up the components of devices 110, 210 and 310 is extremely important. Materials must be chosen which will bear the weight of even the heaviest victim, yet still be light enough to be easily transported to the scene of an accident by emergency medical personnel. It has been found that hollow members preferably of an hexagonal shape will provide sufficient strength and rigidity for the various support rails which form a part of this invention. Particularly, it has been found that high-strength aluminum will provide sufficient strength at low weight. If desired other materials having sufficient strength, rigidity and weight may be used.

If the support rails 12 and 14 are formed from tubing having an hexagonal cross-section the flat sides of the hexagon will assist the jaw assemblies 15 in engaging the various support rails. It will be understood that while tubing having an hexagonal cross-section is shown in the preferred embodiment other cross-sections may be used.

Straps 26 are made from material or fabric having a high tensile strength, good flexibility and minimal stretch under load. This material or fabric is of the type normally used for seat belts or cargo nets. Typically, these type strap assemblies include nylon or other high-strength filaments, but in an emergency situation where time is critical rope may be employed in the place of high strength flexible straps. Chin support 52, risers 54 and nape support 80 may be fabricated from leather or any convenient material having similar properties to leather.

To add the greatest amount of flexibility to the device it is recommended that all components be provided in a kit 90 as shown in FIG. 4. Kit 90 will include a wide variety of component sizes. By including support rails and components of various lengths and sizes, victims of all weights, sizes and shapes may be transported by use of the device of the present invention.

There is therefore provided by the built around body attitude device and method of the present invention a system for simultaneously immobilizing the spinal column and transporting an accident victim having a suspected spinal fracture, irrespective of the size, weight or configuration of the victim.

It is to be understood that while the built around body attitude device has been explained by reference to its preferred embodiments, any changes or modifications to the device which become apparent to those skilled in the art by a reading of the foregoing description are to be included within the scope of the appended claims.

What I claim is:

1. A device for both immobilizing the spinal column of a victim having a suspected spinal fracture and transporting the victim away from the scene of an accident, said device comprising:

an adjustable frame portion substantially in the shape of a rectangle whose size and configuration is determined by the body attitude of the victim at the scene of the accident;

flexible strap means to support the body weight and to suspend and immobilize the spinal column of the victim in the position found at the accident scene, said flexible strap means being adapted to be selectively positioned and interlaced around the victim within said adjustable frame;

whereby when said flexible strap means to support the body weight and to suspend and immobilize the spinal column of the victim are interlaced within said adjustable frame and around the victim, the victim may be transported with an immobilized spinal column.

2. The device as defined in claim 1 wherein said adjustable frame consists of two side support rails and two end support rails.

3. The device as defined in claim 2 wherein said side support rails and said end support rails are formed of aluminum tubing.

4. The device as defined in claim 3 wherein said tubing has a hexagonal cross section.

5. The device as defined in claim 2 wherein said side support rails are connected to said end support rails by openable jaw couplings.

6. The device as defined in claim 1 wherein said flexible means to support the weight of and immobilize the spinal column of the victim is a network of straps.

7. A device for suspending and immobilizing the spinal column of and transporting a victim having a suspected fractured vertebrae comprising:

an adjustable frame portion substantially in the shape of a rectangle whose size and configuration is determined by the body position of the victim, said adjustable frame portion having:
    two side support rails;
    two end support rails;
    means for releasably mounting said side support rails to said end support rails; and
    selectively positionable flexible strap means to adjustably support the body weight and suspend and immobilize the spinal column of the victim interlaced between said side support rails;

whereby when said side support rails are releasably mounted to said end support rails and said flexible strap means which adjustably support the body weight of the victim and immobilize the spinal column are interlaced between said side support rails and around the victim, the completed device fixedly supports the body attitude of the victim and the victim may be transported with an immobilized spinal column.

8. The device as defined in claim 7 wherein said side support rails and said end support rails are hollow.

9. The device as defined in claim 8 wherein said side support rails and said end support rails are formed of aluminum.

10. The device as defined in claim 9 wherein said side support rails and said end support rails are formed in an hexagonal shape.

11. The device as defined in claim 7 wherein said means for releasably mounting said side support rails to said end support rails are openable jaw couplings.

12. The device as defined in claim 7 wherein said flexible means to support the victim and immobilize the spinal column is a network of straps.

13. The device as defined in claim 7 further including ring posts mounted on said side support rails.

14. The device as defined in claim 13 wherein said ring posts are mounted on said side support rails by releasable jaw couplings.

15. The device as defined in claim 7 further including means to support the head of the victim in the position found at the scene of the accident attached to one of said side support rails.

16. A device for transporting and immobilizing the spinal column of a victim in a sitting position with a suspected fractured vertebrae comprising:

a generally rectangular adjustable lower frame adapted to be constructed around the lower extremities of the victim:

an adjustable upright frame adapted to be constructed around the torso of the victim, said upright frame being releasably and tiltably adjustably mounted to said lower frame;

flexible strap means to support the lower extremities of the victim interlaced within said lower frame;

flexible strap means to support the torso of victim interlaced within said upright frame;

whereby when said upright frame is releasably mounted to said lower frame and the victim is interlaced within said frames, the victim may be transported in a sitting position with the spinal column immobilized.

17. The device as defined in claim 16 wherein said frames are formed of hollow tubing.

18. The device as defined in claim 17 wherein said hollow tubing is aluminum.

19. The device as defined in claim 18 wherein said hollow tubing has an hexagonal cross-section.

20. The device as defined in claim 16 wherein said releasable mountings for said upright frame to said lower frame are jaw couplings.

21. The device as defined in claim 16 wherein said flexible means to support the extremities and the torso of the victim is a network of straps.

22. The device as defined in claim 16 further including ring members releasably mounted to said lower frame.

23. The device as defined in claim 16 wherein said upright frame provides for angular positioning with respect to said lower frame.

24. The device as defined in claim 16 further including means to support the head of the victim attached to said upright frame.

25. The device as defined in claim 24 wherein said means to support the head of the victim include a rigid member releasably mounted on said upright frame; a chin support; a nape support and flexible risers extending from said chin support and said nape support to said rigid member.

26. The device as defined in claim 16 wherein said upright frame includes cross members.

27. The device as defined in claim 26 wherein said cross members are split so as to be extensible and rotatable.

28. A method for immobilizing the spinal column of the victim having a suspected fractured vertebrae and transporting the victim from the scene of an accident, said method comprising the steps of:
forming an adjustable frame portion substantially in the shape of a rectangle around the victim of a size and configuration determined by the body attitude of the victim;
immobilizing the victim in the body attitude found at the scene of the accident by adjustably interlacing flexible support strap means around the victim and within said frame;
lifting the victim in an immobilized position by lifting the combination of said adjustable frame and said flexible support strap means with the victim immobilized therein.

29. The method as defined in claim 28 wherein the step of immobilizing the victim in the body attitude found at the scene of the accident further includes the step of immobilizing the position of the head of the victim in the position found at the scene of the accident.

* * * * *